(12) United States Patent
Werner et al.

(10) Patent No.: US 6,192,278 B1
(45) Date of Patent: Feb. 20, 2001

(54) MEDICAL LEAD ADAPTOR

(75) Inventors: Robert L. Werner, Minnetonka; Thomas J. Winkler, Isanti; Ray Gravlin, Coon Rapids, all of MN (US)

(73) Assignee: Medtronic, Inc., Minneapolis, MN (US)

( * ) Notice: Under 35 U.S.C. 154(b), the term of this patent shall be extended for 0 days.

(21) Appl. No.: 09/421,881

(22) Filed: Oct. 21, 1999

Related U.S. Application Data (62) Division of application No. 09/150,434, filed on Sep. 9, 1998, now abandoned, which is a division of application No. 08/846,193, filed on Apr. 25, 1997, now Pat. No. 5,931,861.

(51) Int. Cl.[7] .................................................. A61N 1/02
(52) U.S. Cl. ............................................................. 607/115
(58) Field of Search .................................... 439/909, 729, 439/834, 835; 607/115, 116, 119, 122

(56) References Cited

U.S. PATENT DOCUMENTS

| | | |
|---|---|---|
| 3,188,605 | 6/1965 | Slenker . |
| 4,116,518 | 9/1978 | Pleskac . |
| 4,178,052 | 12/1979 | Ekbom et al. . |
| 4,245,642 | 1/1981 | Skubitz et al. . |
| 4,341,226 | 7/1982 | Peters . |
| 4,466,441 | 8/1984 | Skubitz et al. . |
| 4,545,381 | 10/1985 | Bournay, Jr. et al. . |
| 4,741,704 | 5/1988 | DeLuca . |
| 4,944,088 | 7/1990 | Doan et al. . |
| 4,951,687 | 8/1990 | Ufford et al. . |
| 5,007,435 | 4/1991 | Doan et al. . |
| 5,234,359 | 8/1993 | Takahashi et al. . |
| 5,354,326 | 10/1994 | Comben et al. . |
| 5,931,861 | * 3/1999 | Werner et al. ........................ 607/115 |

* cited by examiner

*Primary Examiner*—George R. Evanisko
(74) *Attorney, Agent, or Firm*—Thomas F. Woods; Harold R. Patton; Girma Wolde-Michael (57) ABSTRACT

A medical lead adaptor that provides a rapid, secure, insulated connection of the lead connector end assembly of a cardiac lead having electrodes adapted to be placed in or on the body with an external medical device is disclosed. The adaptor connector assembly is configured with an elongated receptacle to accept a bipolar, in-line, or a unipolar lead connector end sharing common dimensions. The elongated receptacle includes connector pin and ring receptacle contacts spaced apart from one another therein. In a preferred embodiment, an elongated slot that extends laterally of the elongated receptacle cooperates with a lock mechanism to allow the lateral insertion of the lead connector end assembly, with a stylet wire inserted into the cardiac lead body lumen, into the elongated receptacle. When inserted therein, the lead connector ring and/or pin are nested into contact with the ring and/or pin receptacle contacts and are held there by the lock mechanism. Several embodiments are disclosed of alternate configurations of the elongated receptacle, receptacle contacts and lock mechanism.

4 Claims, 8 Drawing Sheets

MEDICAL LEAD ADAPTOR

CROSS-REFERENCE TO RELATED APPLICATIONS

This application is a continuation of divisional application of U.S. patent application Ser. No. 09/150,434 filed Sep. 9, 1998, now abandoned which, in turn, is a divisional application of co-pending parent U.S. patent application Ser. No. 08/846,193 filed Apr. 25, 1997 for "Medical Lead Adaptor" to Werner et al., now U.S. Pat. No. 5,931,861.

Reference is hereby made to commonly assigned, co-pending U.S. patent application Ser. No. (P-4160) filed on even date herewith, for MEDICAL LEAD ADAPTOR in the names of V. P. Castle et al.

FIELD OF THE INVENTION

The present invention generally relates a medical lead adaptor for making a temporary connection between a medical lead and an external medical device, particularly for making the connection of a permanent or temporary cardiac lead or heart wire with an external cardiac monitor or stimulator, depending on the nature of the implantable cardiac lead or heart wire.

BACKGROUND OF THE INVENTION

The earliest instances of relatively prolonged cardiac stimulation, namely cardiac pacing, of a patient's heart was effected through implanted cardiac leads attached to the heart muscle at distal electrode ends and extended through an incision in the patient's skin. Initially, cardiac pacing was employed during post-operative recovery from cardiac surgery, and the attachment to the heart was made to the epicardium during the surgical procedure. To effect unipolar pacing of the heart, a single such implantable pacing lead was employed in conjunction with a subcutaneously implanted or skin surface attached return electrode coupled to an external lead conductor. To effect bipolar pacing of the heart, two such implantable pacing leads were implanted with the electrode ends implanted a distance apart. Initially, the attachment mechanism typically required a second surgical procedure to remove the distal electrode(s) and the pacing lead(s).

The attachment of the proximal ends of the lead conductors to the temporary cardiac pacemaker connector elements was initially effected by simply stripping insulation from the proximal conductor ends, inserting the bare conductor ends around or through transverse openings in threaded posts, and tightening down thumb nuts. Later, finished connector pins were formed at the proximal connector ends of the lead bodies that could be inserted into end openings of the thumb nuts and connector posts.

Implantable pacing leads evolved into permanent, unipolar and bipolar, endocardial and epicardial, pacing leads for chronic implantation in a patient and with proximal electrical connector assemblies connected with connector elements of a totally implanted, cardiac pacemaker pulse generator. To withstand stress, implantable pacing lead conductors were formed of coiled wire and inserted within an insulative lead body lumen, thereby providing a coiled wire lumen that was sized to receive a stiffening stylet wire to assist transvenous implantation of endocardial pacing leads. The proximal end of the coiled wire conductor was attached to a tubular connector pin at the terminus of the lead connector end shaped to be received in the connector assembly of the implantable pacemaker pulse generator. In the case of endocardial permanent pacing leads, the connector pin was formed with a lumen therein aligned with the coiled wire lumen so that the stiffening stylet wire could be inserted down the length of the lead body, used during the transvenous introduction, and withdrawn after placement of the distal electrode was achieved. Many of these features are employed in current permanent pacing leads.

More recently, bipolar and multi-polar permanently implantable pacing leads and leads for use in pacing and cardioversion/defibrillation (collectively referred to as permanent implantable cardiac leads) have been developed using coaxially arranged, coiled wire conductors and/or parallel-wound, multi-filar coiled wire conductors. In the case of endocardial cardiac leads, the stylet wire lumen is employed to receive the stiffening stylet wire for implantation as described above. The proximal connector end assemblies are formed with at least two spaced apart lead connector elements arranged in-line from a proximal lead connector pin to at least one more distally located ring-shaped element or lead connector ring. Typical bipolar in-line lead connector assemblies for multi-filar, coiled wire conductors are shown, for example, in commonly assigned U.S. Pat. Nos. 4,944,088 and 4,951,687 and 5,007,435, respectively, incorporated herein by reference.

Different manufacturers have produced implantable cardiac leads with lead connector end assemblies that match the connector block terminals of implantable medical devices of the same manufacturer. In recent years, one dimensional pacemaker connector standard has been made implemented, namely the low profile connector "IS-1" standard (ISO 5841-3:1992(E)) for bipolar in-line and unipolar lead connector end assemblies. Other permanent, bipolar, in-line, cardiac lead connector end assemblies conform dimensionally with the MEDTRONIC 3.2 mm low profile connector standard. Certain permanent unipolar cardiac lead connector end assemblies conform dimensionally with the MEDTRONIC 5 mm connector standard.

Unipolar and bipolar, temporary endocardial pacing leads and temporary epicardial heart wires were also developed for implantation of the distal electrode(s) thereof in contact with the endocardium or sutured through the epicardium of the hearts of hospitalized patients. The lead body size of these temporary pacing leads and heart wires has typically been smaller than that of permanent cardiac leads because of the absence of an internal wire coil lumen for receiving a stiffening stylet wire. Still, in the case of bipolar temporary pacing leads and heart wires, either a lead connector pin and ring set having comparable separations apart to those of permanent cardiac leads or bifurcated lead connector assemblies are employed providing a pair of lead connector pins. Exemplary temporary bipolar pacing leads include the MEDTRONIC® TEMPTRON temporary pacing leads having a uniform diameter, in-line, connector pin and ring assembly. Exemplary heart wires include the MEDTRONIC® Model Nos. 6491, 6492, 6494 and 6500 unipolar heart wires and the Model 6495 bipolar heart wire as described in commonly assigned U.S. Pat. No. 4,341,226, incorporated herein by reference.

During a hospitalization, a heart wire or temporary pacing lead of these types may be implanted to allow monitoring and demand pacing of the heart as the patient recovers from cardiac surgery or another condition. In addition, it may be necessary at times to connect the proximal connector end of a permanent cardiac lead already implanted in a patient to a temporary external pacemaker. The proximal connector end assemblies in each case are attached, for example, to external medical device connector elements of MEDTRONIC®

Model Nos. 5348 or 5388 external single chamber or dual chamber cardiac pacemakers. The external medical device connector elements of such external cardiac pacemakers can constitute either spaced RCA type female sockets or a shrouded connector housing that are not compatible with cardiac lead connector end assemblies.

Therefore, when a bipolar heart wire or permanent or temporary pacing lead is to be connected, it is necessary to use a further "patient cable" adaptor to complete the connection. The MEDTRONIC® Model 5433A/V or the Model 5832/S reusable safety cables are employed to make the connection between the temporary pacemaker and the proximal connector ends of the heart wire or temporary pacing lead. Alternatively, the MEDTRONIC® Model 5455/S or the Model 5833/S disposable cable is employed to make the connection between the temporary pacemaker and the proximal connector ends of a temporary pacing lead.

A similar situation arises during a surgical implantation of a pacemaker or pacemaker-cardioverter-defibrillator including a permanent cardiac lead or lead system or the replacement connection of a implantable pulse generator of one of these types with a pre-existing permanent cardiac lead or lead system. During or after implantation of the implantable cardiac lead(s), an external pacing system analyzer, e.g., the MEDTRONIC® Model No. 5311B PSA, is attached to the proximal lead connector end assembly accessible through the incision to assess the performance of the system. Again, the Model 5311B connector elements are not compatible with the lead connector end elements for safety reasons. It is necessary to use either a disposable or a reusable "surgical cable" adaptor to complete the connection. Examples include the MEDTRONIC® Model 5410/S reusable surgical cable and the combination of the MEDTRONIC® Model 5411/S reusable adaptor and Model 5455/S disposable surgical cable.

Some of the above-identified patient and surgical cable adaptors constitute simply a connector assembly at one end that is compatible with the PSA or temporary pacemaker terminals, an external lead body enclosing the external lead conductors, and lead connector element connectors at the other end. Typically, two to four conductors are included in the lead body, and a set of two or four alligator clips are provided at the other ends for attachment to the lead connector ring and pin of one or two implantable cardiac leads.

Other, typically reusable patient and surgical cables employ a mechanism for receiving the proximal connector ends of the heart wire, temporary pacing lead or permanent cardiac lead. For example, either RCA type female sockets are used or a dual thumb screw attachment mechanism is used in the above-referenced MEDTRONIC® Model 5832/S and Model 5433A/V reusable patient cables, respectively.

Commonly assigned U.S. Pat. Nos. 4,245,642 and 4,466,441 disclose medical lead adaptors of the latter type wherein lead connector end assemblies are insertable into sockets of a housing to make electrical contact with a single or two electrical contacts spaced apart therein to receive bifurcated bipolar, in-line bipolar, or unipolar lead connector rings and/or pins. The attachment is effected by tightening down thumb screws to prevent the connector end assemblies from slipping out of the socket openings of the housing in each case. It is not possible to make an attachment with a permanent pacing lead having a stylet wire fitted within the lead lumen and projecting out proximally through the connector pin. This case can only be accommodated by the use of alligator clips that attach across the connector rings and pins.

Such an attachment is not as secure and electrically isolated as would be desirable. It is undesirable to either lose the connection or to allow an electrical static discharge or other shock or impulse to reach the heart through the exposed lead connector ends. At present, it is necessary to loop and tape the assembled adaptor lead and implantable lead body against the patients body and also place tape over the alligator clips.

At times, it has been observed that the careless use of alligator clips can damage the insulation sheathes adjacent to the lead connector end ring or connector pins. In IS-1 leads, damage to the insulating sheath and the seal rings on either side of the connector ring has been observed due to movement of the jaws of the alligator clips.

SUMMARY OF THE INVENTION

It is an object of the present invention to solve these problems identified with prior art methods and mechanisms for attaching an external medical device to an implantable cardiac lead of the types including permanent cardiac leads, temporary pacing leads and heart wires of the types having unipolar lead connector end assemblies or bipolar, in-line, lead connector end assemblies.

The present invention is implemented in several embodiments of a medical lead adaptor having an adaptor connector assembly which provides a rapid and secure connection of the proximal connector end assembly of such an implantable cardiac lead an external medical device of the types described above. The secure attachment of the lead connector end assembly within a connector receptacle of the adaptor connector assembly avoids inadvertent release during patient movement or manipulation of the implantable cardiac lead and the medical lead adaptor. Moreover, the lead connector element(s), i.e., the lead connector ring and/or pin, are electrically isolated within or on the connector receptacle to minimize accidental contact with a conductive surface or medical personnel.

In each preferred embodiment wherein the connection is with a permanently implantable, endocardial cardiac lead, the medical lead adaptor is configured to allow the stiffening stylet wire to remain within the lead lumen and can be employed if necessary to re-position the distal end of the lead while the external medical device remains attached. The secure attachment of the lead connector end assembly avoids inadvertent release during manipulation of the cardiac lead body and stiffening stylet wire. Moreover, the lead connector element(s), i.e., the lead connector ring and/or pin are electrically isolated within a connector receptacle to avoid contact while manipulating the stiffening stylet wire and cardiac lead body.

The medical lead adaptor of the present invention advantageously minimizes inadvertent release of contact with the lead conductor pin and ring attendant to the prior art attachment mechanisms that allowed the use of the stylet wire.

The medical lead adaptor of the present invention also is easily opened and closed without the need to tighten down threaded thumb screws or the like.

The medical lead adaptor of the present invention also advantageously minimizes the possibility of damage to the insulating sleeves of bipolar in-line cardiac lead connector assemblies by ensuring that they can only be inserted in alignment with receptacle contacts within the elongated receptacle.

Moreover, the preferred embodiments of the present invention can be readily re-sterilized using autoclave or ethylene oxide sterilization or other sterilization methods because of their relatively open configurations, allowing re-use of the medical lead adaptors and considerable savings to the medical facility.

In the preferred embodiments, the elongated receptacle in the adaptor connector assembly is shaped to receive the lead connector end assembly in a nesting manner so that it cannot axially move therein. A locking mechanism is provided for locking the lead connector end assembly in the elongated receptacle so that the lead connector elements are in contact with the receptacle contacts in a locked position. The lead connector end assembly is laterally inserted or withdrawn through an elongated slot when the locking mechanism is manipulated to an open position. If a stiffening stylet is present in the implantable cardiac lead, the stylet wire projecting proximally from the lead connector end assembly is laterally inserted or withdrawn with the lead connector end assembly. A variety of adaptor connector assemblies are disclosed in preferred embodiments of the invention illustrating exemplary configurations of elongated receptacles, receptacle contacts, and locking mechanisms for performing these functions.

In the first preferred embodiment, the implantable lead body and the external lead body extend in opposite directions away from opposite ends of the adaptor connector assembly. A locking clip closes the laterally extending slot in a housing through which the lead connector assembly and the stylet wire are inserted into the elongated receptacle. Therefore, the lead connector end assembly is securely attached within the elongated receptacle of the adaptor connector assembly even if one or the other of the opposed lead bodies are accidentally pulled on.

BRIEF DESCRIPTION OF THE DRAWINGS

These and other objects, advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS

The present invention is implemented in a number of embodiments of medical lead adaptor connector assemblies that each provide a rapid and secure connection of the proximal lead connector end assembly of a cardiac lead of the types described above with an external medical device of one of the types described above. In each medical lead adaptor embodiment, an adaptor connector assembly is coupled to an external lead body having one or preferably two external electrical conductors therein each extending between a first external lead conductor end to a second external lead conductor end at the second end of the external lead body. Each first external lead conductor end is electrically connected with an electrical contact within the connector receptacle adapted to receive and make electrical contact with a cardiac lead connector element. Each second lead conductor end is coupled with an external lead connector element of an external lead connector assembly for making electrical contact with the connector element of the external medical device. It is contemplated that a variety of such medical lead adaptors with differing external lead connector end assemblies adapted to fit the connector elements of differing external medical devices may be necessary.

In each medical lead adaptor embodiment of the present invention, the adaptor connector assembly is configured to accept a permanent cardiac lead connector end assembly with a stiffening stylet wire extending proximally thereof. It is also contemplated that the adaptor connector assembly may alternatively receive the lead connector ends of other permanent cardiac leads not employing a stiffening stylet wire. In addition, it is contemplated that temporary pacing leads and heart wires that share compatible lead connector element dimensions, that is, compatible spacing between and diameters of ring connector and/or pin connector elements may also be received in the adaptor connector assembly.

However, the lead connector end assemblies of permanent pacing leads, particularly, older lead models already implanted in patients, are not consistent in dimensions, e.g. the spacing between and diameters of the ring and pin connector elements of bipolar, in-line pacing leads. It therefore may be necessary to provide a variety of medical lead adaptors in accordance with the present invention with compatibly dimensioned connector receptacles and spaced apart receptacle contacts for different lead types. Similarly, it may be necessary to provide a variety of medical lead adaptors with compatibly dimensioned connector receptacles and receptacle contacts to accommodate the pin and/or ring lead connector elements of various types of heart wires and temporary pacing leads.

The first preferred embodiment of the medical lead adaptor 10 for making a rapid electrical connection between an external medical device connector assembly (not shown) and a proximal lead connector end assembly 12 of an implantable cardiac lead 14 is shown in FIGS. 1–7. The medical device connector assembly may take any of the forms used with the above-referenced MEDTRONIC® Model 5311B PSA or Model 5348 and 5388 temporary pacemakers. The proximal portion of the implantable cardiac lead 14 is shown in part and includes an elongated implantable lead body 16 extending from the lead connector end assembly 12 toward the distal cardiac lead end (not shown). The distal cardiac lead end includes at least one electrode implanted in contact with a heart chamber of the patient 20, and may take any of the known forms for implantable cardiac leads of the type described above. The implantable lead body 16 contains an implantable lead conductor coupled between a distal electrode and a proximal lead connector element of the lead connector end assembly 12.

Figure 1:
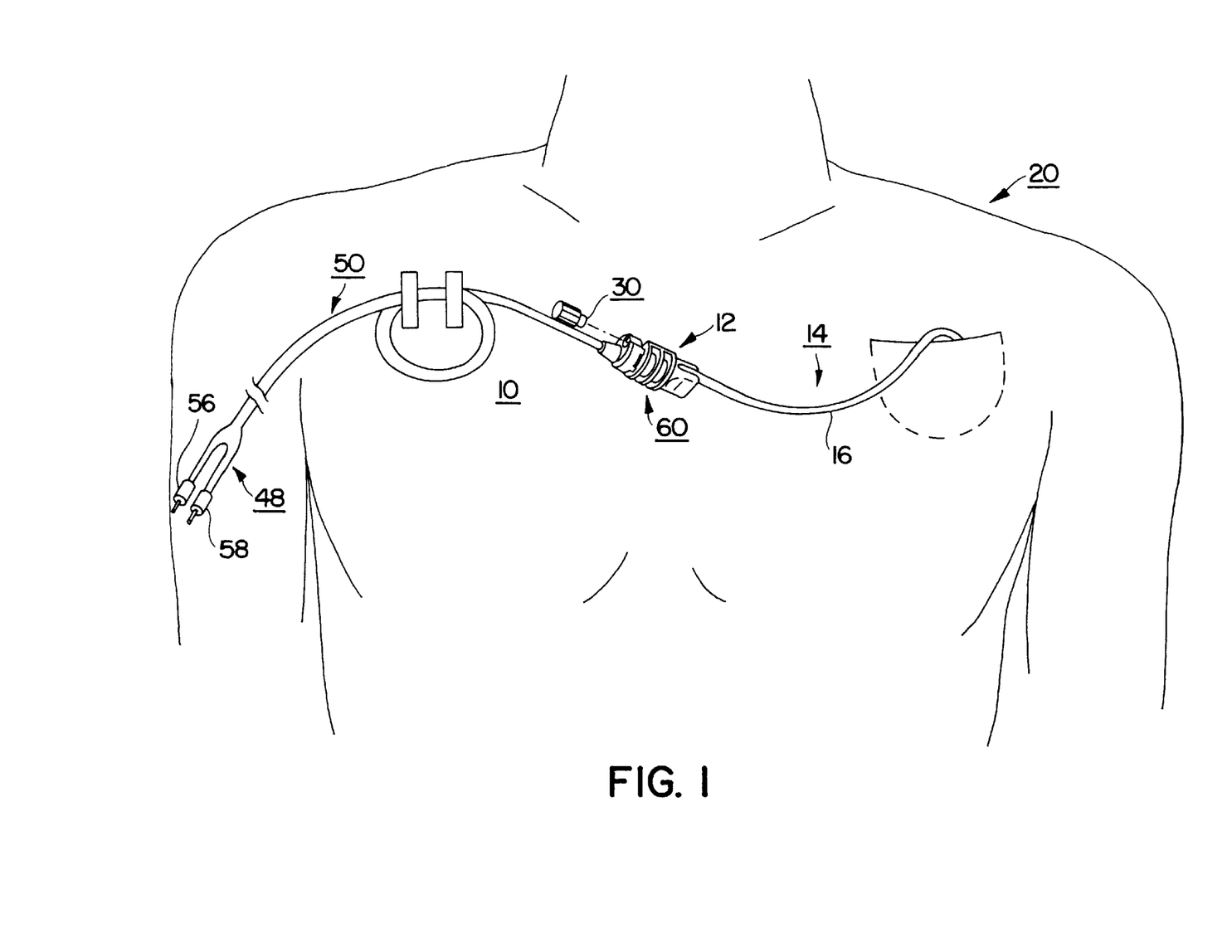
FIG. 1 is a simplified schematic view of an implanted permanent cardiac lead of the types described above implanted in a patient and coupled to the adaptor connector assembly of the medical adaptor of the first preferred embodiment of the present invention.
Figure 2:
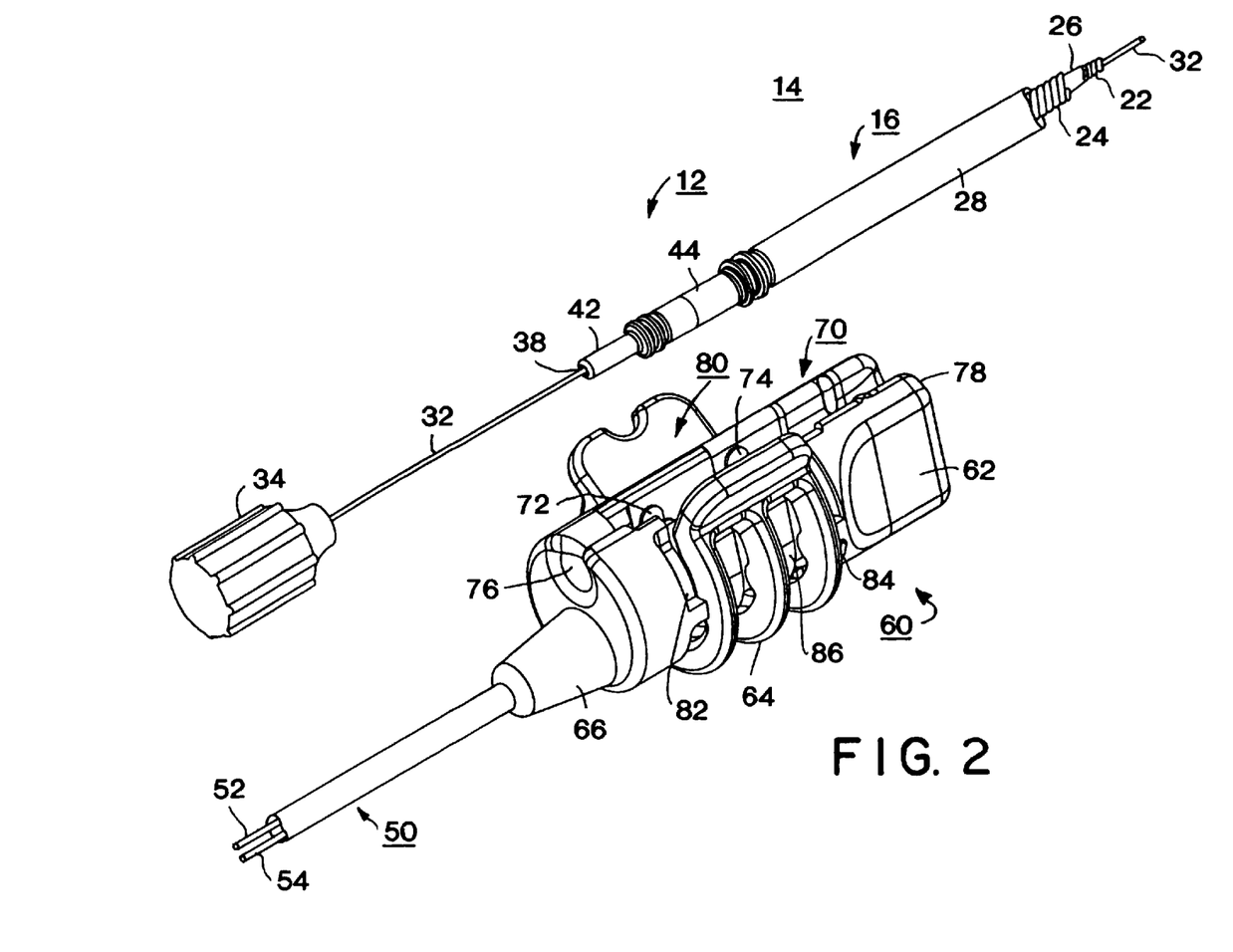
FIG. 2 is an exploded isometric partial view of the proximal end of a permanent cardiac lead oriented to be inserted into the connector receptacle of the adaptor connector assembly of the medical lead adaptor of the first preferred embodiment of the present invention.
Figure 3:
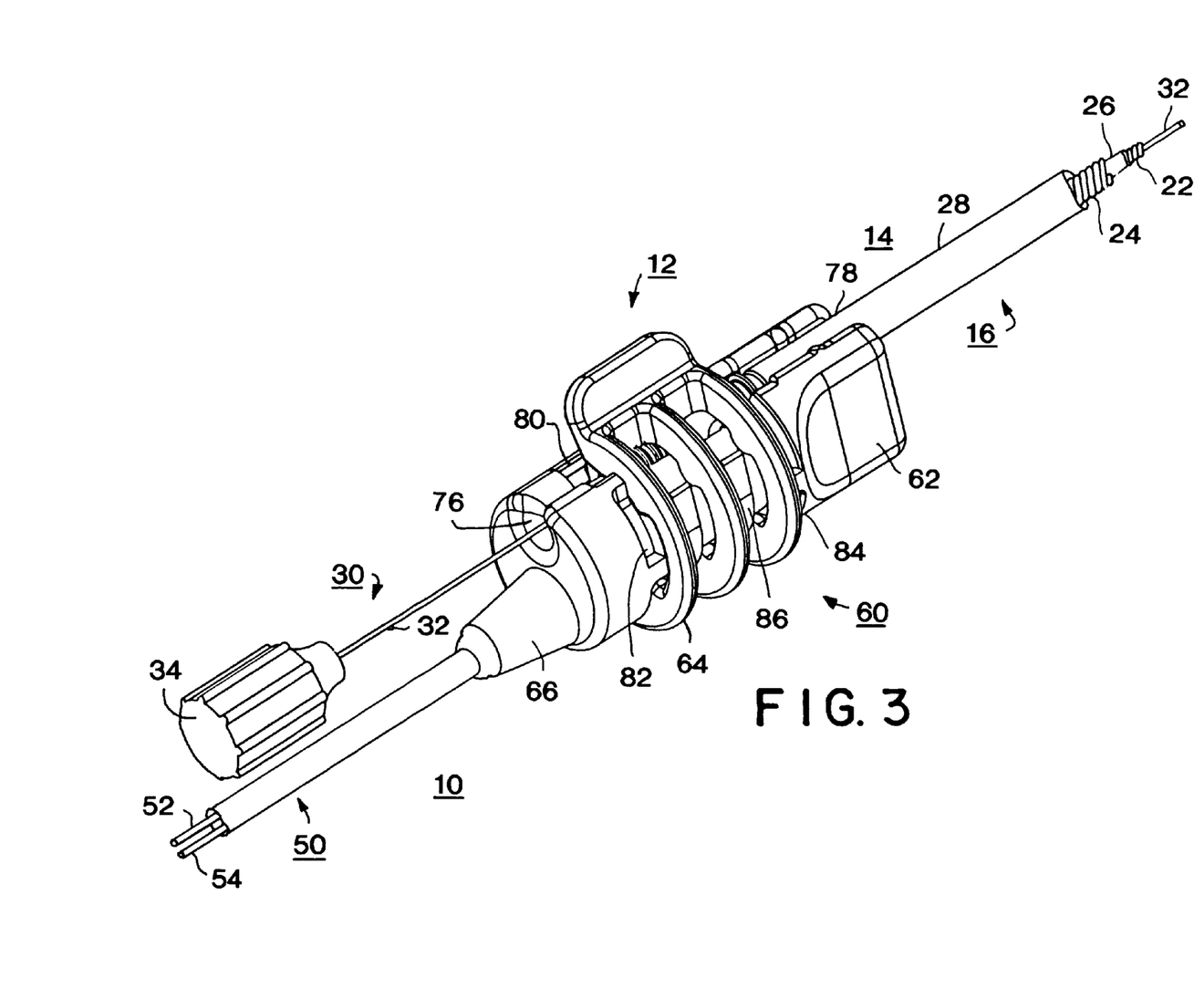
FIG. 3 is an isometric partial view of the proximal end of a permanent cardiac lead inserted into the connector receptacle of the adaptor connector assembly of the first preferred embodiment of the present invention.
Figure 4:
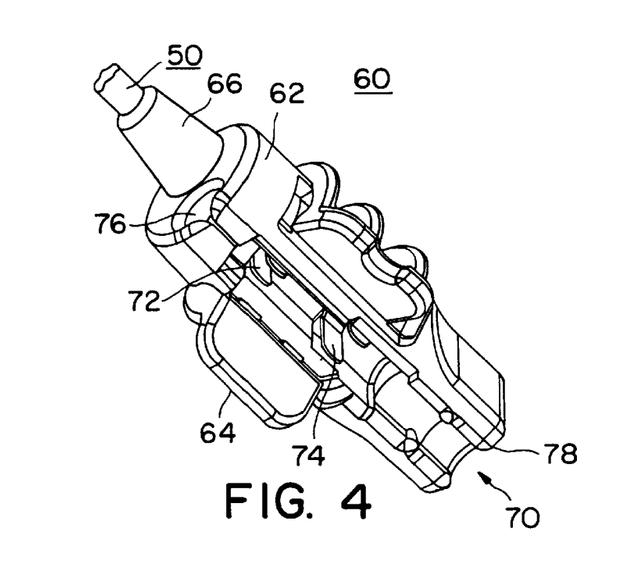
FIG. 4 is an isometric partial view of the adaptor connector assembly of the first preferred embodiment of the present invention.
Figure 5:
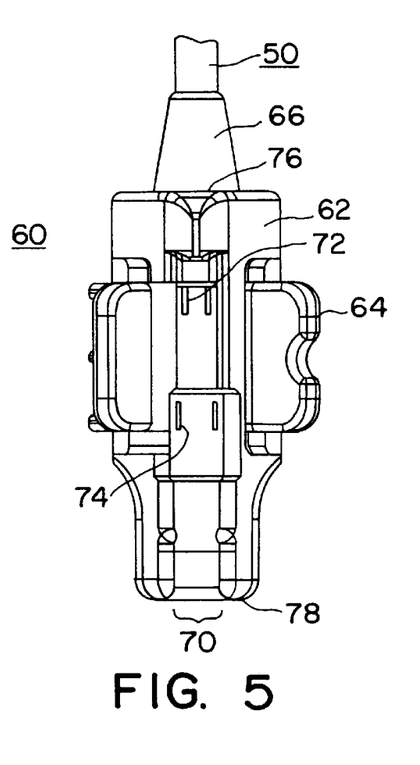
FIGS. 5–7 are top, side and end partial views of the adaptor connector assembly of FIG. 3.
Figure 6:
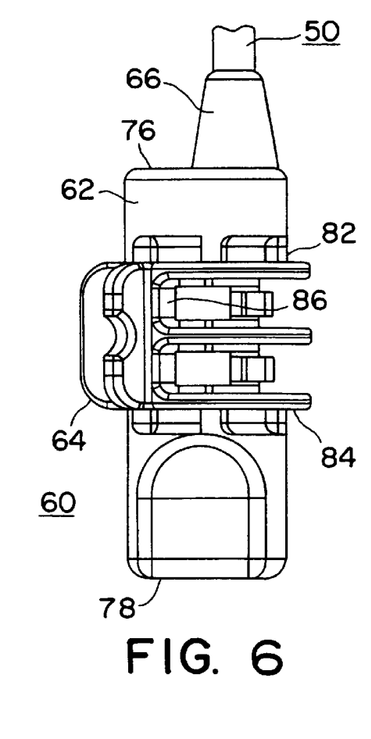
Figure 7:
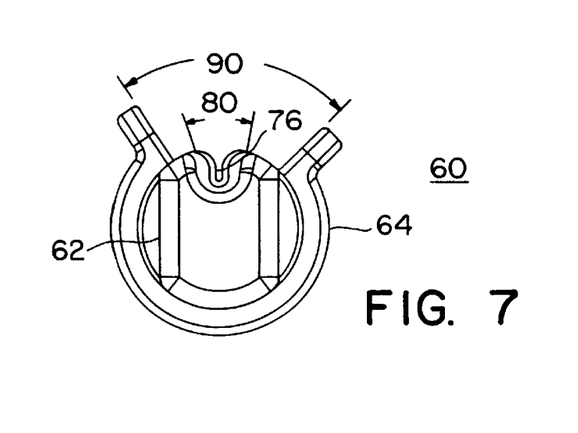

For purposes of illustration convenience, the implantable cardiac lead 14 is depicted as a bipolar, in-line, permanent cardiac pacing lead employing co-axially wound, coiled wire, implantable lead conductors 22 and 24 separated apart by an insulating sheath 26 and included within an outer insulating sheath 28. The outer implantable lead conductor 24 is coupled to a respective lead connector ring 44, and the inner implantable lead conductor 22 is coupled to a respective lead connector pin 42. These connections may be effected in the manner shown, for example, in the above-incorporated 5,007,435 patent. A lumen is formed within the inner implantable lead conductor 22 for receiving a stiffening stylet wire 32 through a lumen end opening 38 in the lead connector pin 42. When the stylet wire 32 is received in the lumen, it extends proximally from the lumen end opening 38 so that the stylet knob 34 may be manipulated to rotate or axially extend or withdraw the stylet wire 32 with respect to the lead body lumen.

The medical lead adaptor 10 includes an external lead body 50 having at least one external electrical conductor therein extending between first and second external lead conductor ends thereof. Preferably, the external lead body 50 encases two electrically isolated external electrical conductors 52 and 54 of any known configuration which are coupled at their ends with two external lead connector elements of an external lead connector assembly 48. The external lead connector assembly 48 may be of any of the types described above for making electrical contact with the external medical device terminals, e.g., the bifurcated connector pins 56 and 58 shown in FIG. 1 or a shrouded connector assembly.

An adaptor connector assembly 60 for receiving the lead connector end assembly 12 is formed at the other end of the external lead body 50 and includes a housing 62 and a rotatable lock mechanism or clip 64. The housing 62 is generally tubular having a generally cylindrical outer surface extending between proximal and distal housing ends 76, 78 thereof. The housing 62 includes the elongated receptacle 70 (best shown in FIGS. 4 and 5) that extends from the proximal and distal housing ends 76 and 78 and is shaped to conformably receive the lead connector end assembly 12 when laterally inserted therein through a receptacle slot 80. At least the lead connector ring 44 and pin 42 of the lead connector end assembly 12 are received in the elongated receptacle 70 between the proximal and distal housing ends 76, 78 so that they are not exposed.

The elongated receptacle 70 includes first or proximal and second or distal receptacle contacts 72 and 74 positioned along the base and extending up the opposed sides of the elongated receptacle 70 for making electrical contact with lead connector pin 42 and ring 44, respectively. Each receptacle contact 72, 74 is formed of thin spring metal formed in a U-shape and is attached at the base thereof to one of the first external lead conductor ends extending through the strain relief 66 and within the housing 62. In each case, the base is also attached to the base of the elongated receptacle 70 and spaced apart to match the distance between the lead connector pin 42 and ring 44. The opening widths of the receptacle contacts 72 and 74 are sized to accommodate and be slightly expanded by the diameters of the respective lead connector end pin 42 and ring 44.

The receptacle slot 80 extends laterally of the elongated receptacle 70 to the exterior housing surface for receiving the lead connector end assembly having the stylet wire 32 extending proximally from the lumen end opening 38. The receptacle slot 80 is narrowed adjacent to the proximal housing end 76 so that only the stylet wire 32 may be passed through it. The lead connector end assembly 12 and stylet wire 32 are shown in FIG. 2 poised to be inserted into the elongated receptacle 70 laterally through receptacle slot 80. The lead connector end assembly 12 is shown disposed in the elongated receptacle 70 with the proximally extending stylet wire extending through the proximal end opening of the proximal housing end 76 in FIG. 3.

The rotatable locking clip 64 must be in the open position depicted in FIGS. 2 and 4–7 in order to insert or withdraw the lead connector assembly 12 from the elongated receptacle 70. In this open position, an elongated clip slot 90 defined by the parallel opposed ends of the rotatable locking clip 64, is aligned with the receptacle slot 80 to provide lateral access through the aligned clip slot 90 and receptacle slot 80. The proximal lead connector end assembly 12 and stylet wire 32 are retained in the elongated receptacle 70 by the rotation of the rotatable locking clip 64 with respect to the housing 62 from the open position to the closed or locked position depicted in FIGS. 1 and 3. In the closed and locked positions, the clip slot 90 is no longer aligned with the receptacle slot 80 and elongated receptacle 70.

An exterior surface circumferential track 86 is formed around the circumference of the tubular housing 62 in order to retain and guide movement of the rotatable locking clip 64. The outer surface circumferential track 86 is defined by first and second spaced apart rails 82 and 84 extending around the circumference of the housing 62 having rail diameters exceeding the track surface diameter therebetween. The locking clip 64 is generally C-shaped and cylindrical and has an internal tracking surface that conforms with the outer surface circumferential track in width and diameter and is rotatable about the tubular housing 62 between the locked and open positions. In this manner, the lock mechanism has an inner diameter that is sized with respect to the rail diameters and the track surface diameter to be restrained by the spaced apart rails 82, 84 and to allow relative rotation of the locking clip 64 about the outer surface circumferential track 86.

In use, the locking clip 64 is grasped and rotated while the tubular housing 62 is grasped on opposite sides near the distal end 78 to hold it stationary. Through this rotation, the elongated clip slot 90 is alignable with the receptacle slot 80 on rotation of the lock mechanism 64 to the open position. In the open position, the implantable lead connector end assembly 12 and stylet wire 32 extending proximally therefrom are inserted or withdrawn laterally through the aligned clip slot 90 and receptacle slot 80 into or from the elongated receptacle 70. In the closed position, the locking clip 64 locks the implantable lead connector end assembly 12 in the elongated receptacle 70 assuring secure electrical contact between a receptacle contact 72, 74 and a corresponding lead connector pin 42 and ring 44. The stylet wire 32 may be withdrawn, inserted or manipulated because the locking clip 64 in the locked position assures that the manipulation will not disturb the electrical contact or expose the lead connector end ring and pins.

The first preferred embodiment may also be used without the presence of the stylet wire 32 or may be used with epicardial cardiac leads, temporary pacing leads or heart wires that do not have a lumen for receiving a stiffening stylet 30.

The remaining FIGS. 8–26 depict further embodiments of the adaptor connector assembly of the medical lead adaptor of the present invention wherein at least certain features of the first embodiment are incorporated therein. In each illustrated embodiment, the external medical lead adaptor connector assembly 160, 260, 360 and 460 provides for a rapid electrical connection between a medical device connector assembly and a proximal lead connector end assembly 12 of an implantable cardiac lead 14. The implantable cardiac lead takes the form of lead 14 described above with respect to the first embodiment depicted in FIG. 2 and is of the type having an elongated implantable lead body 16 extending from the lead connector end assembly toward the distal cardiac lead end. In particular, the implantable lead body 16 contains first and second spaced apart implantable lead conductors coupled to proximal and distal lead connector end ring 44 and pin 42 as described above. The implantable lead body 16 has a lumen formed therein for receiving a stylet wire 32 through a lumen end opening 38 in the connector end pin 42. The stylet wire, when received in the lumen, extends proximally from the lumen end opening 38 so that the stylet wire 32 may be turned or moved in and out to manipulate the distal end of the implantable medical lead in a manner well known in the art. Each of the embodiments depicted in FIGS. 8–26 are adapted to receive 5 such a bipolar, in-line implantable lead connector end assembly 12 in an elongated receptacle 170, 270, 370, 470 with the stylet wire 32 in the lead lumen and extending proximally to be manipulated in this manner. Again, a unipolar implantable lead connector end assembly sharing the same dimensions may be received in the elongated receptacle and make an electrical connection with the 1o proximal receptacle contact 172, 272, 372 or 472. And the elongated receptacles 170, 270, 370, 470 may receive such lead connector end assemblies without a stylet 30 in place. The stylet 30 may also be withdrawn entirely or inserted into the lead lumen while the lead connector end assembly 12 is received in the elongated receptacle 170, 270, 370, 470.

FIGS. 8–13 illustrate the second preferred embodiment of a medical lead adaptor 110 in accordance with the invention wherein the lock mechanism is effected by the spring material and form of the proximal and distal receptacle contacts 172 and 174. The external lead body 150 has at least first and second external electrical conductors therein each extending between a first external lead conductor end thereof to a second external lead conductor end. The external lead body 150 is formed with an external lead connector assembly 148 that is particularly configured for making electrical contact indirectly with an external medical device connector assembly (not shown) through a further medical lead adaptor or cable. The external lead terminals 156 and 158 of the external lead connector assembly 148 are electrically connected to the second ends of the external lead conductors within the external lead body 150. The external lead terminals 156 and 158 have electrically exposed flat surfaces bordered by insulating ridges for placement between the jaws of alligator clips of a further medical lead adaptor or cable. This particular external lead connector assembly 148 may be employed in any of the embodiments of he invention.

An adaptor connector assembly 160 is coupled to the external lead body 150 for receiving the lead connector end assembly (not shown) and for making electrical contact between the first and second implantable lead conductors and first ends of the first and second external electrical conductors, respectively. The adaptor connector assembly 160 further includes a generally rectangular housing 162 having parallel side and proximal and distal end walls defining an elongated receptacle 170. The elongated receptacle 170 is shaped to conformably receive the lead connector pin 42 and ring 44 of the lead connector end assembly 12 when inserted therein through a side wall opening defining a receptacle slot 180. The elongated receptacle 170 includes the first, or proximal, and second, or distal, receptacle contacts 172 and 174 positioned along said elongated receptacle 170 for making electrical contact with the lead connector pin 42 and ring 44, respectively.

A proximal end opening 176 formed in the proximal end of the housing 162 receives the stylet wire extending proximally from the lead lumen end opening when the implantable cardiac lead connector end assembly 12 and stylet wire 32 are laterally inserted through the receptacle slot 180 into the receptacle 170. A distal end opening 178 formed in the distal end of the housing 162 receives the lead body 16 extending distally from the lead connector end assembly 12 when the lead connector end assembly 12 is laterally inserted through the receptacle slot 180 into the receptacle 170.

Figures 8, 9, 11, 12, 13:
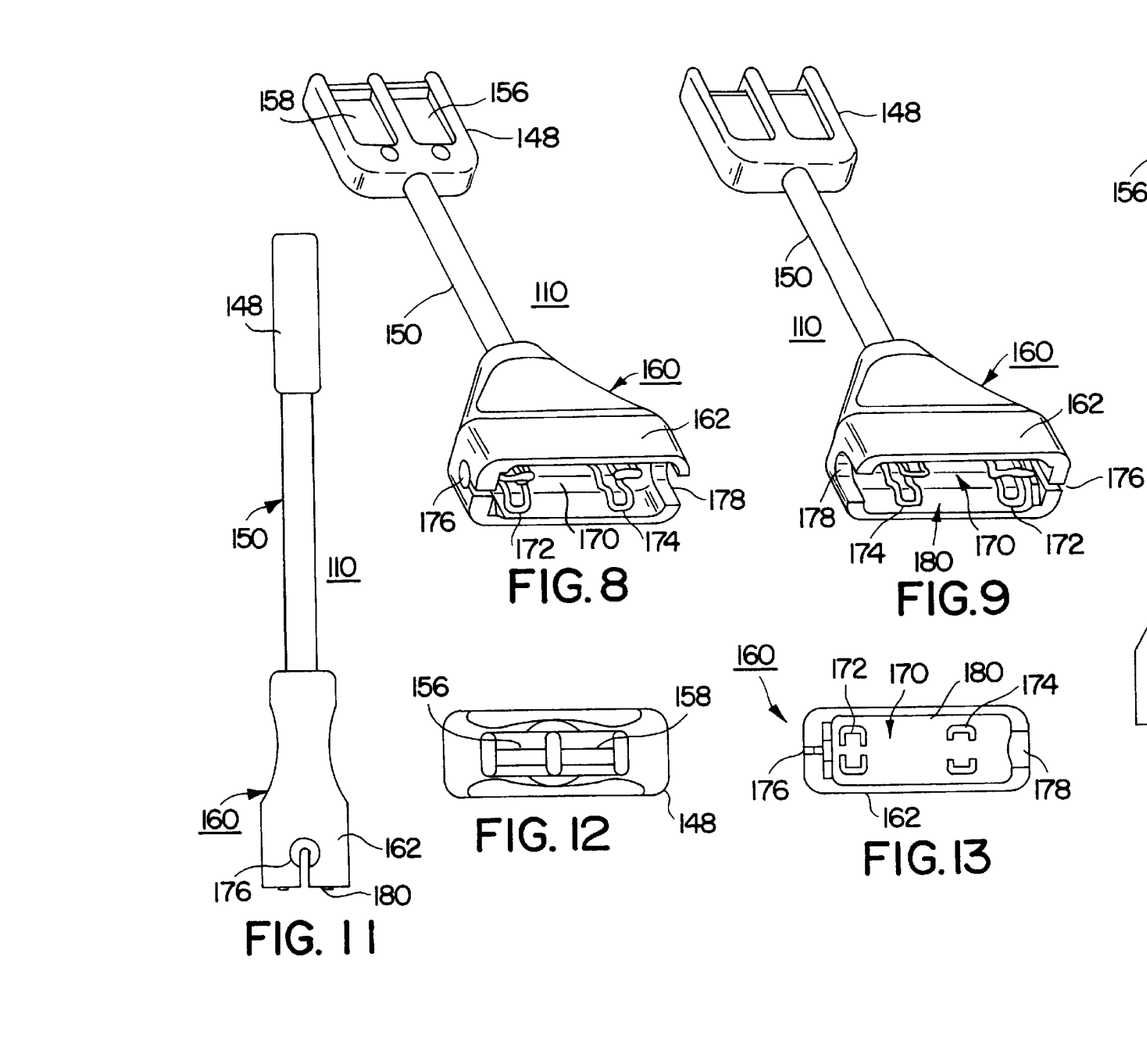
FIGS. 8 and 9 are first and second isometric side views of a second preferred embodiment of a medical lead adaptor in accordance with the invention.
FIGS. 10–13 are plan, side, and opposite end views of the second preferred embodiment of the medical lead adaptor depicted in FIGS. 8 and 9.
Figure 10:
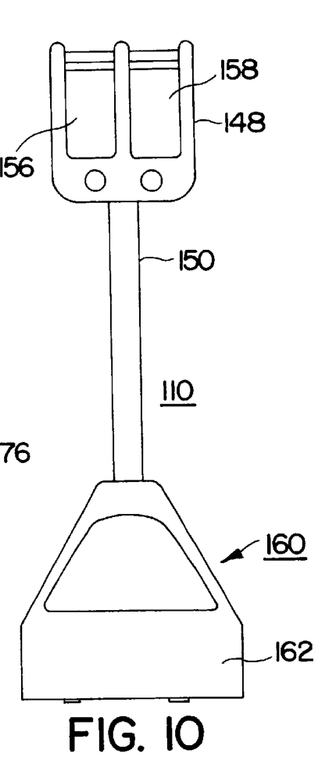

The first, or proximal, and second, or distal, receptacle contacts 172 and 174 are each formed of a conductor wire spring material formed in a generally U-shape and are spaced apart within the elongated receptacle 170 as depicted in FIGS. 8, 9 and 13. Each receptacle contact 172 and 174 has a base section extending to first and second opposed branch sections that are positioned across from one another that terminate in free ends that are spaced apart to each define slot widths when relaxed. The free ends are also flared apart from the terminal slots as shown in the figures. The terminal slot widths are less than the widths of the respective receptacle connector pin an ring and do not allow the respective lead connector elements to pass therethrough. However, the terminal slots of receptacle contacts 172 and 174 may be widened to allow the respective connector pin 42 and ring 44 to pass therethrough as they are pressed against the flared apart free ends. The opposed branch and base sections are dimensioned to tightly engage the lead connector pin 42 and ring 44 when they are received in the elongated receptacle 170 in the locked position and thereby provide the lock mechanism.

FIGS. 14–18 depict a third preferred embodiment of a medical lead adaptor connector assembly 260 in accordance with the invention. For convenience of illustration, neither the external lead connector assembly coupled to an end of the external lead body 250 nor the external electrical conductors therein for making the electrical connection with the external medical device are shown in FIGS. 14–18.

The adaptor connector assembly 260 is coupled to the external lead body 250 through a strain relief 266. The adaptor connector assembly 260 receives the lead connector end assembly 12 (not shown) for making electrical contact between the first and second implantable lead conductors and first ends of the first and second external electrical conductors, respectively. The adaptor connector assembly 260 further includes generally arcuate and elongated housing halves 262 and 262' formed of insulating material each defining opposed portions of an elongated receptacle 270. The housing halves 262 and 262' extend between proximal and distal ends to define proximal and distal end openings 276 and 278 of the elongated receptacle 270. The housing halves 262 and 262' are formed along the ends of first and second lever arms 292 and 294, respectively. The elongated receptacle 270 is further defined by the proximal and distal receptacle contacts 272 and 274 which are arcuately shaped to conformably receive the lead connector pin 42 and ring 44 of the lead connector end assembly 12 when inserted therein.

Figures 14, 15, 16:
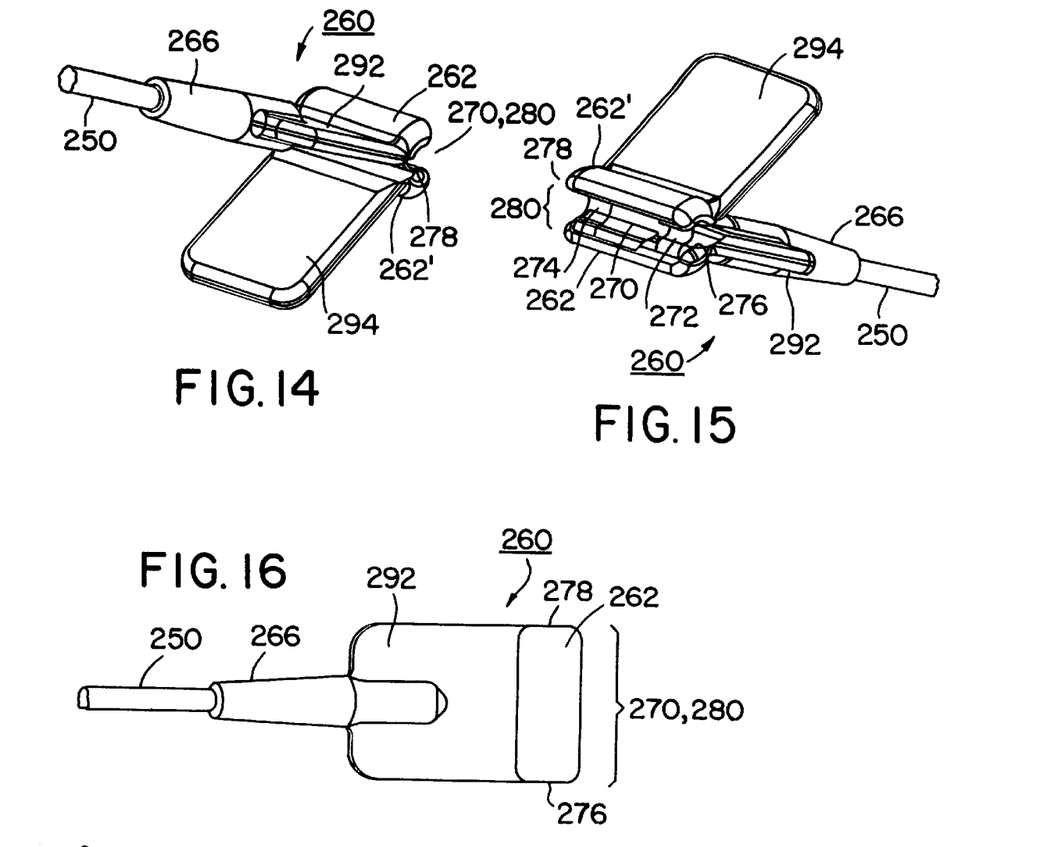
FIGS. 14 and 15 are first and second isometric side views of a third preferred embodiment of a medical lead adaptor connector assembly in accordance with the invention.
FIGS. 16–18 are top, side, and end views of the third preferred embodiment of the medical lead adaptor connector assembly depicted in FIGS. 14 and 15.
Figure 18:
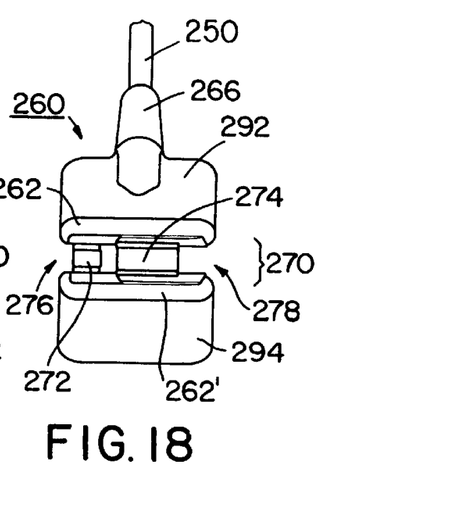

The elongated receptacle 270 includes the first or proximal and second or distal receptacle contacts 272 and 274 positioned along said elongated receptacle 270 for making electrical contact with the connector pin 42 and ring 44, respectively. The proximal and distal receptacle contacts 272 and 274 are each formed of a flat, thin, conductive spring material formed in a generally arcuate shape in the elongated receptacle 270 as depicted in FIGS. 15 and 18. The elongated receptacle 270 is otherwise relatively open at both ends and along the interior side thereof between the housing halves 262 and 262'. The flat, thin, conductive spring material of each of the receptacle contacts 272, 274 is bent and extends for lengths away from the elongated receptacle 270 enclosed within the relatively flat, first and second lever arms 292 and 294. Thus, the proximal and distal receptacle contacts 272 and 274 effectively connect the first and second lever arms together and, with the housing halves 262 and 262', define the elongated receptacle 270. The receptacle contacts 272 and 274 are electrically connected to first and second external lead conductors in external lead body 250 through connections made within the lever arm 292.

The first and second receptacle contacts 272 and 274 are dimensioned to tightly engage the connector pin 42 and ring 44, respectively, when positioned in the elongated receptacle 270 in the locked position. The spring strength of the flexible elongated housing 262 and the U-shaped proximal or first and distal or second receptacle contacts 272 and 274 provide the lock mechanism through pressure applied radially about the lead connector end assembly 12 fit tightly within the elongated receptacle 270.

The proximal end opening 276 receives the stylet wire 32 extending proximally from the lead lumen end opening 38 when the implantable cardiac lead connector end assembly 12 and stylet wire 32 are laterally inserted through the slot 280 into the receptacle 270. The distal end opening 278 receives the lead body 16 extending distally from the lead connector end assembly 12 when it is laterally inserted through the slot 280 into the receptacle 270.

The elongated lateral slot 280 extends along the space separating the housing halves 262 and 262' having a slot width that does not allow the lead connector end assembly 12 to be passed through it in the closed and locked positions.

Figure 17:
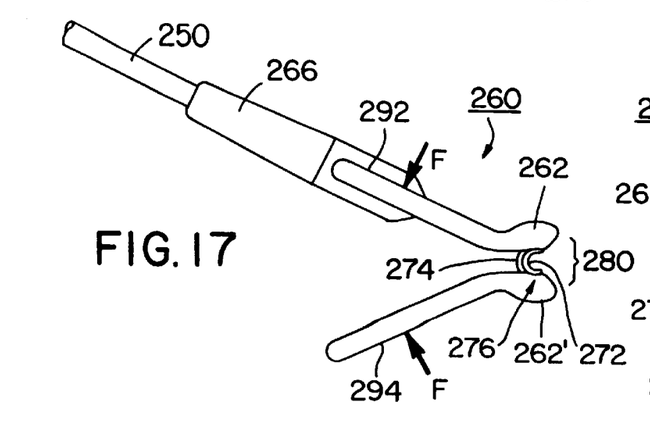

In this way, the lead connector assembly 12 is locked into the elongated receptacle 270 and cannot slip laterally out of the slot 280 after it is inserted through it. In order to allow the lead connector assembly 12 to be laterally passed through the lateral slot 280, a mechanism for increasing the slot width is provided. This unlock feature of the lock mechanism comprises the first and second lever arms 292 and 294 attached at fixed arm ends to the elongated housing halves 262 and 262' along opposite edges of the lateral slot 280 and extending laterally away from it. The free ends are separated by a closed or locked position distance, whereby force applied to the free ends thereof in the direction of the arrows F shown in FIG. 17 is transmitted to the fixed arm ends causing the width of the lateral slot 280 to be increased to the open position. After the force F is released, the opening width of slot 280 decreases to the closed position depicted in FIGS. 14–18 or a locked position embracing a lead connector end assembly 12 in the elongated receptacle 270.

Figures 19, 20, 21:
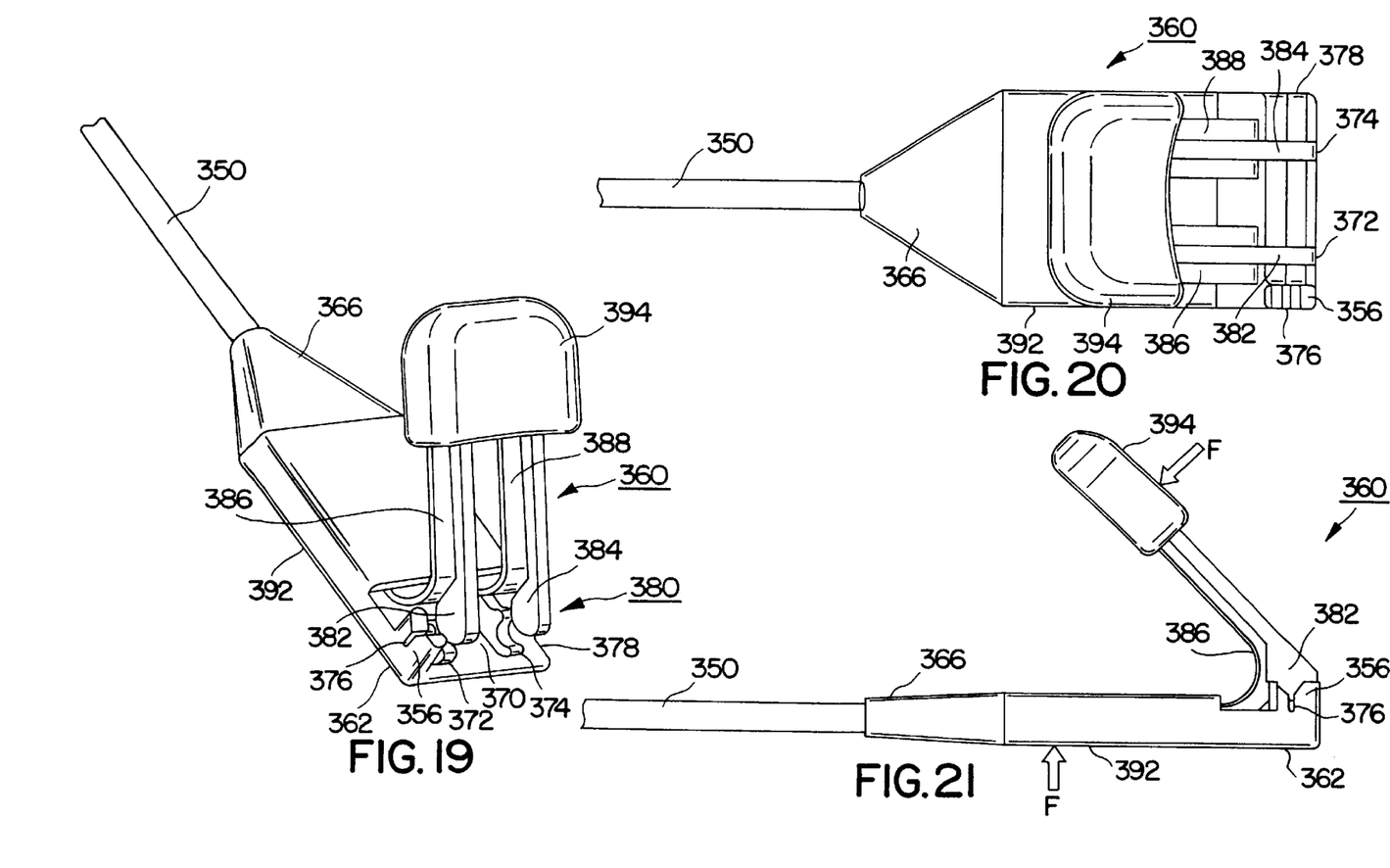
FIG. 19 is an isometric side view of a fourth preferred embodiment of a medical lead adaptor connector assembly in accordance with the invention.
FIGS. 20 and 21 are top and side views of the fourth preferred embodiment of the medical lead adaptor connector assembly depicted in FIG. 19.

FIGS. 19–21 depict a fourth preferred embodiment of a medical lead adaptor connector assembly 360 in accordance with the invention. In these figures, the external lead connector assembly coupled to an end of the external lead body 350 and the external electrical conductors therein for making the electrical connection with the external medical device are again not shown for convenience. This embodiment is a variation on the third embodiment, wherein the lock mechanism is effected by spring loaded force beams 382 and 384 acting against the connector pin 42 and ring 44 when the lead connector end assembly 12 is fitted in the receptacle 370.

An adaptor connector assembly 360 is coupled to the external lead body 350 through a strain relief 366. The adaptor connector assembly 360 receives the lead connector end assembly 12 (not shown) for making electrical contact between the first and second implantable lead conductors and first ends of the first and second external electrical conductors, respectively. The adaptor connector assembly 360 further includes a generally flat housing 362 of insulating material providing an elongated receptacle 370 and first or proximal and second or distal receptacle contacts 372 and 374. The elongated receptacle 370 also includes the upstanding proximal receptacle end 356 shaped with a stylet wire receiving proximal end opening 376. The elongated receptacle 370 is relatively open and shaped to conformably receive the lead connector pin 42 and ring 44 of the lead connector end assembly 12 when inserted therein through a laterally extending slot 380 opened when the lock mechanism is displaced to the open position. The receptacle 370 includes the first, or proximal, and second, or distal, receptacle contacts 372 and 374 positioned along said elongated receptacle 370 for making electrical contact with the lead connector pin 42 and ring 44, respectively.

The proximal end opening 376 formed in the proximal end tab 356 receives the stylet wire 32 extending proximally from the lead lumen end opening 38 when the implantable cardiac lead connector end assembly 12 and stylet wire 32 are laterally inserted into the receptacle 370. A distal end opening 378 formed in the distal end of the housing 362 receives the lead body 16 extending distally from the lo lead connector end assembly 12 when it is laterally inserted into the receptacle 370 when the lock mechanism is displaced to provide the lateral slot 380.

The proximal and distal receptacle contacts 372 and 374 are each formed of saddle shaped conductive material formed to have generally arcuate shaped contact surfaces and are spaced apart within the elongated receptacle 370 as depicted in FIGS. 19 and 20. The receptacle contacts 372 and 374 are electrically connected to first and second external lead conductors in external lead body 350. The arcuate, exposed, contact surface of the receptacle contacts 372 and 374 generally conforms in diameter with the cylindrical surface diameter of the respective connector pin 42 and ring 44, respectively. The arcuate, exposed, contact surface of the receptacle contacts 372 and 374 effectively define the elongated receptacle 370.

In order to allow the lead connector assembly 12 to be laterally passed through the receptacle slot 380 and into the elongated receptacle 370, a lock mechanism for increasing the slot width is provided. This lock mechanism comprises first and second lever arms 392 and 394 attached together at fixed arm ends along leaf springs 386 and 388. The housing 362 and the above-described components are formed at one fixed end of the lever arm 392. The lever arm 394 is coupled to one end of the force beams 382 and 384, the other ends of which are spaced from the arcuate surfaces of the receptacle contacts 372 and 374, respectively. The spacing is established by the leaf springs 386 and 388. Force applied in the directions of arrows F to the free ends of the lever arms 392 and 394 compresses the ends of the leaf springs 386 and 388 and separates the force beams 382 and 384 from the proximal and distal receptacle contacts 372 and 374 causing the width of the slot 380 to be increased to the open position. In the open position, the lead connector end assembly 12 and the stylet wire 32 can be laterally inserted or withdrawn through the receptacle slot 380. After the force is released, the receptacle slot 380 width decreases to the closed position shown in FIGS. 19–21 or a locked position with the lead connector end assembly locked into the elongated receptacle 370.

Figures 22, 25:
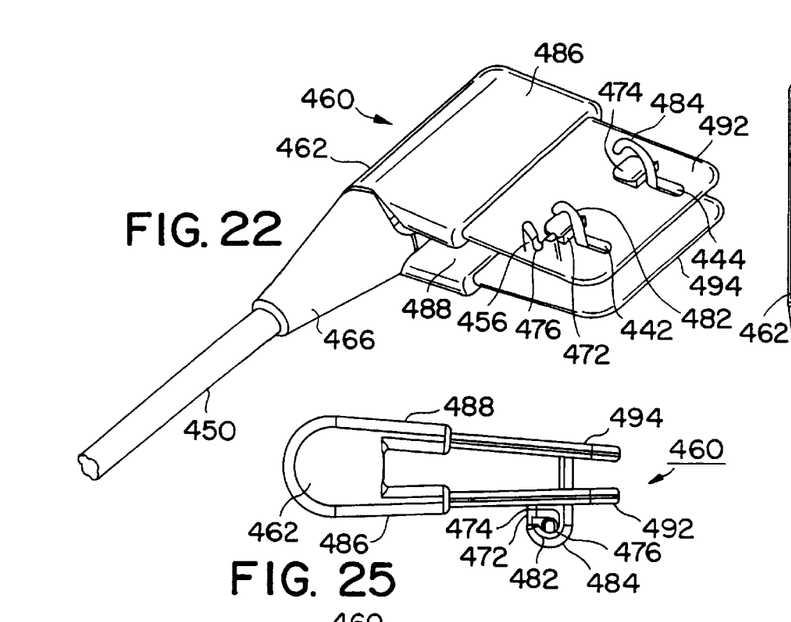
FIG. 22 is an isometric side view of a fifth preferred embodiment of a medical As lead adaptor connector assembly in accordance with the invention.
FIGS. 23–25 are side and end views of the fifth preferred embodiment of the medical lead adaptor connector assembly depicted in FIG. 22 in the closed position of the lock mechanism.
Figure 23:
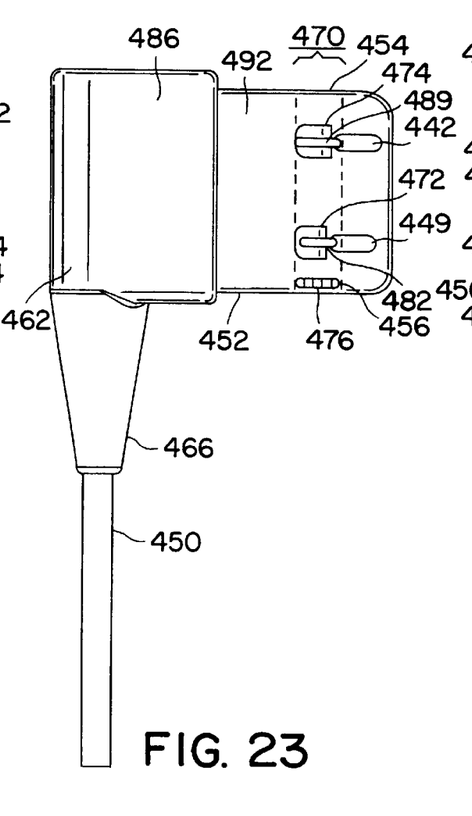

FIGS. 22–26 depict a fifth preferred embodiment of a medical lead adaptor connector assembly 460 in accordance with the invention. For convenience of illustration, the external lead connector assembly coupled to an end of the external lead body 450 and the external electrical conductors therein for making the electrical connection with the external medical device are not shown in FIGS. 22–26. In this embodiment, the elongated receptacle 470 of the lead adaptor connector assembly 450 shown within broken lines in FIG. 23 is aligned axially and offset in parallel relation with the axis of the external lead body 450 approximating the axial alignment of the first embodiment. As in the first embodiment, force applied on one is transmitted axially to the other of the implantable lead body (not shown) or the external lead body 450. The formation and operation of the elongated receptacle 470 and the lock mechanism is somewhat inversely related to those of the third and fourth embodiments. In this embodiment, the lock mechanism is effected by proximal and distal spring loaded force hooks 482 and 484, respectively, that bear against the connector pin 42 and ring 44 nested in the proximal and distal receptacle contacts 472 and 474, respectively. The spring loading is effected by a torsion spring around and within the generally tubular body 462.

The adaptor connector assembly 460 is coupled to the external lead body 450 through a strain relief 466 and tubular body 462. Generally planar wings or tabs 492 and 494 extend from the tubular body 462 through planar spring ends 486 and 488, respectively. The surface of tab 492 forms a generally flat housing of electrically insulating material defining the bounds of the elongated receptacle 470 extending across the flat housing surface from a proximal edge 452 to a distal edge 454 thereof. The elongated receptacle 470 includes the first or proximal and second or distal receptacle contacts 472 and 474 mounted to the surface of tab 492 and spaced apart to comply with the spacing of the lead connector pin 44 and ring 42. The elongated receptacle 470 also includes the proximal receptacle end 456 extending upward from the proximal edge 452 and shaped with a stylet wire receiving proximal end opening 476. The elongated receptacle 470 is relatively open, and shaped to conformably receive the lead connector pin 42 and ring 44 of the lead connector end assembly 12 when inserted therein through a lateral receptacle slot 480 when the lock mechanism is displaced to the open position as shown in FIG. 26.

Figure 24:
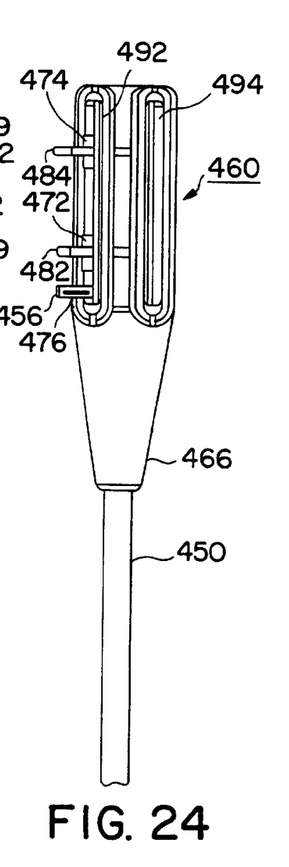

The first and second receptacle contacts 472 and 474 are each formed of conductive material formed to have contact surfaces and are spaced apart within the elongated receptacle 370 as depicted in FIGS. 22–24. The first and second receptacle contacts 472 and 474 are each dimensioned and shaped to engage the connector pin 42 and ring 44 to prevent them from moving laterally when positioned in the elongated receptacle 470 in the locked position. The first and second receptacle contacts 472 and 474 are electrically connected through insulated conductors within tab 492 to first and second external lead conductors of external lead body 450 within the generally tubular body 462.

The proximal end opening 476 formed in the upstanding proximal receptacle end 456 shaped with a stylet wire receiving proximal end opening 476 that receives the stylet wire 32 extending proximally from the lead lumen end opening 38 when the implantable cardiac lead connector end assembly 12 and stylet wire 32 are laterally inserted into the receptacle 470. The distal end of the elongated receptacle 470 at distal side 454 is open and allows the lead body 16 to extend distally from the lead connector end assembly 12 when it is laterally inserted into the elongated receptacle 470 through the lateral receptacle slot 480.

Figure 26:
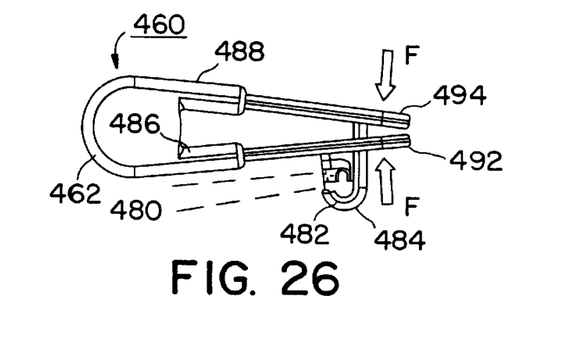
FIG. 26 is an end view of the fifth preferred embodiment of the medical lead adaptor connector assembly depicted in FIG. 22 in the open position of the lock mechanism.

In order to allow the lead connector assembly 12 to be laterally passed through the lateral receptacle slot 480 and into the elongated receptacle 470, the lock mechanism is displaced from the closed position of FIG. 25 to the open position of FIG. 26. The lock mechanism further comprises the first and second force hooks 482 and 484 which apply force against the respective proximal connector pin 42 and ring 44 when they are seated against the respective first and second receptacle contacts 472 and 474. The first and second force hooks 482 and 484 have curved free ends and fixed ends that are attached to the interior surface of the tab 494.

The curved free ends of the first and second force hooks 482 and 484 are extended through the first and second respective openings 422 and 424 through the tab 492 have curved free ends and fixed ends that are attached to the interior surface of the tab 494. Thus, as force is applied in the direction of the arrows F to squeeze the tabs 492 and 494 toward one another shown in FIG. 26, the proximal and distal force hooks 482 and 484 are separated apart from the proximal and distal receptacle contacts 472 and 474, respectively. This depicted open position of the lock mechanism widens the lateral receptacle slot 480. In the open position, the lead connector end assembly 12 and the stylet wire 32 can be laterally inserted or withdrawn through the receptacle slot 480. After the force F is released, the opening of receptacle slot 480 decreases to the closed position of FIG. 25 or the locked position with a lead connector end assembly 12 locked in the elongated receptacle 470.

In each of the above-described embodiments, an external lead body 50, 150, 250, 350, 450 is disclosed enclosing the two external conductors that extend between the receptacle contacts in the respective adaptor connector assembly to an external lead connector element 48. It will be understood that the external lead connector element may take any form that is compatible with the terminals of the external medical device. It is also contemplated that the external lead body and external lead connector element may be replaced by simple external connector assembly formed integrally with the external lead connector assembly 60, 160, 260, 360, 460 to be attached directly to the external medical device terminals. In this case, the external conductors would each extend a short distance between the receptacle contact and the external connector element.

The preceding specific embodiments are illustrative of the practice of the invention. It is understood therefore that other expedients and equivalents of disclosed components or functions known to those of skill in the art or otherwise disclosed herein may be employed in practicing the invention without departing from the invention or the scope of the following claims. In this regard, the particular shape of the lead connector end assemblies and the lead connector elements incorporated therein may take any form or arrangement that may be matched in a complementary fashion by the components forming the elongated receivers. Similarly, the form, number and spacing of the contact terminals for making contact with the lead connector elements may be modified to be compatible therewith and serve the purposes described above.

The illustrated preferred embodiments are described in the context of a bipolar cardiac lead that may be implanted in or applied on the body of a patient having an in-line connector end assembly. It will be understood that the present invention may be implemented in unipolar medical lead adaptors having only a single external lead conductor, receptacle contact and related components for receiving a unipolar lead connector end assembly. Conversely, it will be understood that the features of the present invention may be replicated in an elongated receptacle and receptacle contacts coupled with respective external conductors for receiving tri-polar or other multi-polar, in-line, lead connector end assemblies.

Moreover, it is contemplated that the elongated receptacle in each embodiment may be dimensioned and configured to receive bipolar and unipolar cardiac lead connector end assemblies that conform with the IS-1 standard or conform to the above-referenced "3.2 mm" connector end assembly, for example. One of the dimensional differences between these two bipolar lead connector end assemblies is the separation between the connector pin and ring. The preferred embodiments described above may be modified by providing a common proximal receptacle contact for contacting the connector pin of each type of lead connector end assembly and two distal receptacle contacts each spaced from the pin receptacle contact. The spacing and shape of each distal receptacle contact conforms to the IS-1 and 3.2 mm spacing and ring outer diameter. Both of the distal electrical contacts are electrically connected in common with an external conductor. In this manner either type of lead connector end assembly may be accommodated in the same adaptor connector assembly 60, 160, 260, 360, 460. By logical extension, the same configuration of an adaptor connector assembly may be effected to accommodate differing lead connector end assemblies.

In addition, the present invention may be employed in medical lead adaptors for making connections between other implantable or external medical leads and external medical equipment. For example, a medical lead adaptor may be configured following the above-described principles of the present invention to make electrical connections between implantable nerve, muscle or brain stimulation electrode bearing leads and external stimulators or test equipment.

The various embodiments of the present invention and the variations and equivalents described herein may also be incorporated into a single medical lead adaptor for having multiple adaptor connector assemblies attached in combination with an external lead body and external lead connector assembly. For example, it is envisaged that a single medical lead adaptor for use with a dual chamber pacing lead system may employ two such adaptor connector assemblies for making connection with atrial and ventricular lead connector end assemblies. The first and second receptacle contacts of each adaptor connector assembly are coupled with separate external conductors and to separate terminals of the external connector assembly. The external connector assembly may take any of the known forms for making electrical connection with the atrial and ventricular terminals of the external medical device.

The present invention further includes within its scope methods of using the medical lead adaptors of the present invention.

In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures.

We claim:

1. An adaptor for making a rapid electrical connection between an external medical device and an implantable cardiac pacing lead having an elongated lead body extending between a proximal lead end and a distal lead end, a pacing lead connector at the proximal end of the pacing lead body, an electrode at the distal end of the pacing lead body, first and second spaced apart pacing lead conductors extending within the pacing lead body and coupled to first and second spaced apart connector elements of the pacing lead connector, and a lumen extending within the pacing lead body to receive a stylet wire that can be manipulated by a control element at the end of a portion of the stylet wire that extends proximally of the lumen opening, comprising:

a. an adaptor lead body having first and second electrical conductors extending between a proximal end and a distal end;

b. a connector at the proximal adaptor lead body end adapted for making an electrical connection to an external medical device;

c. an adaptor connector body at the distal adaptor lead body end adapted to mate with the lead connector at the proximal end of the pacing lead body and establish an electrical connection between the first and second pacing lead connector elements and the first and second adaptor lead conductors, said adaptor connector body comprising:

(i) a housing of flexible insulating material having an elongated receptacle extending across a substantially planar surface thereof between a proximal side edge, a distal side edge, and a lateral side edge and being shaped to conform to the profile of the pacing lead connector so as to accept insertion of the pacing lead connector and permit the portion of a stylet wire extending proximally of the lead lumen to remain accessible for manipulation following insertion of the pacing lead connector, said housing including an opening disposed adjacent the proximal side edge through which the portion of a stylet wire extending proximally of the lead lumen opening is received upon insertion of the lead connector;

(ii) first and second contacts positioned along the receptacle so as to be spaced apart between the housing surface proximal and distal side edges for making electrical contact with the first and second pacing lead connector elements upon insertion of the pacing lead connector into the receptacle, said receptacle contacts being formed of a conductive material and being dimensioned so as to engage and restrict lateral movement of the pacing lead connector elements seated against them;

(iii) a separate electrical connection between the first receptacle contact and the first adaptor lead conductor and between the second receptacle contact and the second adaptor lead conductor; and (iv) a locking mechanism disposed adjacent the receptacle and manipulatable between an open position and a closed position, said locking mechanism when in the open position allowing a pacing lead connector and stylet wire extending proximally from the pacing lead lumen to be inserted laterally into the receptacle and to be withdrawn laterally therefrom and when in the closed position locking the pacing lead connector therein with a secure electrical contact between each receptacle contact and a corresponding pacing lead connector element while allowing manipulation of the stylet wire with respect to the lead lumen, said locking mechanism including first and second force hooks to apply and release force with respect to pacing lead connector elements seated against the first and second receptacle contacts.

2. A lead adaptor in accordance with claim 1, wherein the housing further includes:

an elongated, substantially arcuate body portion forming first and second legs;

a first substantially flat tab extending from the first leg of the arcuate body portion, said first tab forming the substantially planar surface, the proximal side edge, the distal side edge, and the lateral side edge; and a second substantially flat tab extending from the second leg of the arcuate body portion, said second tab forming a substantially planar surface, a proximal side edge, a distal side edge, and a lateral side edge spaced apart from the lateral side edge of the first substantially flat tab;

wherein the first and second force hooks each have a fixed end portion attached to the contacts second substantially flat tab and a curved free end portion aligned with a respective one of the first and second receptacle contacts, said curved free end portions and the receptacle forming a receptacle slot through which the pacing lead connector can be passed; and further comprises:

a spring mechanism extending between the legs of the arcuate body portion and the first and second substantially flat tabs to normally maintain the lateral side edges of the tabs spaced apart in the absence of applied force in actuation of the locking mechanism to the closed position having the curved free end portions of the force hooks maintain the pacing lead connector in the receptacle with a secure electrical contact between each receptacle contact and a corresponding pacing lead connector element while allowing force applied against the tabs to move the lateral side edges of tabs in actuation of the locking mechanism to the open position having the curved free end portions of the force hooks move away from the receptacle contacts to open the receptacle slot and allow the pacing lead connector and stylet wire extending proximally from the lead lumen to be inserted into or withdrawn from the elongated receptacle.

3. An adaptor for making a rapid electrical connection between an external medical device and an implantable cardiac pacing lead having an elongated lead body extending between a proximal lead end and a distal lead end, a pacing lead connector at the proximal end of the pacing lead body, an electrode at the distal end of the pacing lead body, at least one pacing lead conductor extending within the pacing lead body and coupled to a corresponding connector element of the pacing lead connector, and a lumen extending within the pacing lead body to receive a stylet wire that can be manipulated by a control element at the end of a portion of the stylet wire that extends proximally of the lumen opening, comprising:

a. an adaptor lead body having at least one electrical conductor extending between a proximal end and a distal end;

b. a connector at the proximal adaptor lead body end adapted for making an electrical connection to an external medical device;

c. an adaptor connector body at the distal adaptor lead body end adapted to mate with the lead connector at the proximal end of the pacing lead body and establish an electrical connection between each pacing lead connector elements and a corresponding adaptor lead conductor, said adaptor connector body comprising:

(i) a housing of flexible insulating material having an elongated receptacle extending across a substantially planar surface thereof between a proximal side edge, a distal side edge, and a lateral side edge and being shaped to conform to the profile of the pacing lead connector so as to accept insertion of the pacing lead connector and permit the portion of a stylet wire extending proximally of the lead lumen to remain accessible for manipulation following insertion of the pacing lead connector, said housing including an opening disposed adjacent the proximal side edge through which the portion of a stylet wire extending proximally of the lead lumen opening is received upon insertion of the lead connector;

(ii) at least one contact positioned along the receptacle between the housing surface proximal and distal side edges for making electrical contact with the corresponding pacing lead connector element upon insertion of the pacing lead connector into the receptacle, said receptacle contact being formed of a conductive material and being dimensioned so as to engage and restrict lateral movement of the pacing lead connector element seated against it;

(iii) a separate electrical connection between each receptacle contact and each adaptor lead conductor; and (iv) a locking mechanism disposed adjacent the receptacle and manipulatable between an open position and a closed position, said locking mechanism when in the open position allowing the pacing lead connector and the stylet wire extending proximally from the pacing lead lumen to be inserted laterally into the receptacle and to be withdrawn laterally therefrom and when in the closed position locking the pacing lead connector therein with a secure electrical contact between each receptacle contact and the corresponding pacing lead connector element while allowing manipulation of the stylet wire with respect to the lead lumen, said locking mechanism including first and second force hooks to apply and release force with respect to the corresponding pacing lead connector element seated against each receptacle contacts.

4. A lead adaptor in accordance with claim 3, wherein the housing further includes:

an elongated, arcuate body portion forming first and second legs;

a first substantially flat tab extending from the first leg of the arcuate body portion, said first tab forming the substantially planar surface, the proximal side edge, the distal side edge, and the lateral side edge; and a second substantially flat tab extending from the second leg of the arcuate body portion, said second tab forming a substantially planar surface, a proximal side edge, a distal side edge, and a lateral side edge spaced apart from the lateral side edge of the first substantially flat tab;

wherein each force hook has a fixed end portion attached to the second substantially flat tab and a curved free end portion aligned with a corresponding one of each receptacle contact, each curved free end portion and each corresponding receptacle contact forming a receptacle slot through which the pacing lead connector can be passed ; and further comprises:

a spring mechanism extending between the legs of the arcuate body portion and the first and second substantially flat tabs to normally maintain the lateral side edges of the tabs spaced apart in the absence of applied force in actuation of the locking mechanism to the closed position having the curved free end portion of each force hook maintain the pacing lead connector in the receptacle with a secure electrical contact between each receptacle contact and the corresponding pacing lead connector element while allowing force applied against the tabs to move the lateral side edges of tabs in actuation of the locking mechanism to the open position having the curved free end portion of each force hook move away from each corresponding receptacle contact to open the receptacle slot and allow the pacing lead connector and stylet wire extending proximally from the lead lumen to be inserted into or withdrawn from the elongated receptacle.

\* \* \* \* \*